United States Patent
Luzzi et al.

(10) Patent No.: US 6,190,699 B1
(45) Date of Patent: Feb. 20, 2001

(54) METHOD OF INCORPORATING PROTEINS OR PEPTIDES INTO A MATRIX AND ADMINISTRATION THEREOF THROUGH MUCOSA

(75) Inventors: Louis A. Luzzi, Narragansett; Thomas E. Needham, Wakefield; Zia Hossein, Kingston, all of RI (US); Polireddy Dondeti, New York, NY (US)

(73) Assignee: NZL Corporation, Wakefield, RI (US)

( * ) Notice: Under 35 U.S.C. 154(b), the term of this patent shall be extended for 0 days.

(21) Appl. No.: 09/074,778

(22) Filed: May 8, 1998

(51) Int. Cl.[7] .................................. A61K 9/14; A61K 9/50
(52) U.S. Cl. ..................... 424/489; 424/484; 424/487; 424/499
(58) Field of Search .................................. 424/486, 484, 424/487, 499, 489, 501

(56) References Cited

U.S. PATENT DOCUMENTS

| | | | |
|---|---|---|---|
| 4,226,848 | * 10/1980 | Nagai et al. | 424/19 |
| 4,598,006 | 7/1986 | Sand . | |
| 4,613,500 | * 9/1986 | Suzuki et al. | 429/85 |
| 4,678,684 | 7/1987 | Sand . | |
| 4,818,540 | 4/1989 | Chien et al. . | |
| 4,820,752 | 4/1989 | Berens et al. . | |
| 4,985,242 | * 1/1991 | Sekine et al. | 424/85 |
| 5,043,280 | 8/1991 | Fischer et al. . | |
| 5,112,804 | * 5/1992 | Kowarski | 514/3 |
| 5,169,433 | 12/1992 | Lindsay et al. . | |
| 5,179,079 | * 1/1993 | Hansen et al. | 514/4 |
| 5,183,663 | 2/1993 | Greiner . | |
| 5,183,802 | 2/1993 | Aliverti et al. . | |
| 5,204,108 | * 4/1993 | Illum | 424/434 |
| 5,439,686 | 8/1995 | Desai et al. . | |
| 5,514,670 | 5/1996 | Friedman et al. . | |
| 5,635,216 | * 6/1997 | Thompson | 424/501 |
| 5,977,241 | * 11/1999 | Koloski et al. | 524/502 |

OTHER PUBLICATIONS

"Encapsulation and Controlled Release", D.R. Karsa and R.A. Stephenson, edictors, Royal Society of Chemistry, London, 1993, pp. 117–130.

* cited by examiner

*Primary Examiner*—Thurman K. Page
*Assistant Examiner*—S. Tran
(74) *Attorney, Agent, or Firm*—Hudak & Shunk Co., LPA

(57) ABSTRACT

The present invention describes a surprising new and effective pharmaceutical composition comprising microparticles and a pharmaceutically acceptable carrier. In particular, the present invention describes a pharmaceutical composition containing microparticles off a matrix material into which is infused a therapeutic agent. The present invention further provides a method of infusing a therapeutic agent such as a protein or peptide into a matrix material to form microparticles containing said therapeutic agent by employing a compressed solvent which is normally gaseous at ambient temperature and pressure. A method is also disclosed of treating or preventing a disease in a mammal by administering to said mammal through a mucosal membrane an effective amount of a pharmaceutical composition comprising microparticles containing a therapeutic agent which effectively treats the disease or disorder.

25 Claims, 6 Drawing Sheets

METHOD OF INCORPORATING PROTEINS OR PEPTIDES INTO A MATRIX AND ADMINISTRATION THEREOF THROUGH MUCOSA

FIELD OF THE INVENTION

The present invention provides a surprisingly new and effective pharmaceutical composition comprising a microparticle and a pharmaceutically acceptable carrier. In particular, the present invention provides a pharmaceutical composition containing microparticles 10 to 250 μm in diameter, that serve as the matrix material, which are infused with a therapeutic agent. The present invention further provides a method of infusing a therapeutic agent into a matrix material to form a microparticle containing said therapeutic agent. Specifically, the present invention provides a method of infusing a therapeutic agent which may be a peptide or protein into a matrix material to form a microparticle. A method of treating or preventing a disease in a mammal by administering to said mammal an effective amount of a pharmaceutical composition comprising microparticles containing a therapeutic agent which effectively treats the disease or disorder against which the agent is directed. If desired, a pharmaceutically acceptable carrier may also be employed. The composition of this invention may be administered through a mammalian mucous membrane.

BACKGROUND OF THE INVENTION

Therapeutic agents can be administered to mammals using a variety of techniques. The bioavailability of a therapeutic agent and its effectiveness are often a result of the method used to administer the agent. The most popular method of administering therapeutic agents is orally. Oral administration is popular because it is non-invasive and the therapeutic agent is often readily absorbed into the bloodstream of the recipient. Furthermore, the ease of administration results in enhanced patient compliance. However, despite the many advantages of oral administration, therapeutic agents containing proteins and peptides often cannot be given orally. This is primarily due to proteolytic enzymes present in the gastrointestinal tract which can easily degrade the proteins or peptides, resulting in poor bioavailability of the therapeutic agent. As a result, many therapeutic agents which contain proteins and peptides are delivered parenterally.

Parenteral administration bypasses the gastrointestinal tract and delivers the peptides or proteins directly into the bloodstream and the surrounding tissues of the recipient. This method of administration, however, has several disadvantages. For example, when peptides and proteins are delivered parenterally, they may exhibit an extremely short biological half life. As a result, repeated injections of the necessary peptide or protein are usually required. Furthermore, because parenteral administration is often an invasive therapy, poor patient compliance often occurs. Thus, many patients do not receive an adequate dose of the required therapeutic agent.

An alternative method to parenteral administration of a therapeutic agent is mucosal, especially intranasal administration. The mucosa, such as the nasal membrane, offers more absorption potential than any other noninvasive routes for peptides and proteins. For example, the nasal cavity offers both pharmacokinetic and pharmaceutical advantages. In addition, intranasal administration bypasses the metabolic administration pathways of the gastrointestinal tract and liver and thereby prevents degradation of the peptide or protein within the gastrointestinal tract. Furthermore, the nasal mucosa contains a large surface area and relatively low enzymatic degradation resulting in the rapid absorption of the peptide or protein. Because intranasal administration is both convenient and noninvasive, high patient compliance occurs.

Although there are numerous advantages to intranasal administration relative to parenteral and oral administration, several factors limit the exploitation of the nasal route for systemic absorption of peptides and proteins. For example, because the surface mucus coat in the nose is rapidly cleared, the time period available for therapeutic agent absorption is relatively short. Furthermore, high molecular weight peptides and proteins are not easily absorbed through the nasal membrane due to the lack of permeability. As a result, peptides and proteins are often administered with permeation enhancement compounds to increase bioavailability of the therapeutic agents. These enhancers often result in adverse side effects to the mucus membrane and may disrupt nasal functions. In addition, adverse pathological conditions may affect the nasal functions significantly and disrupt the ability to administer therapeutic agents intranasally. Furthermore, the presence of proteolytic enzymes in the nasal cavity may cause degradation of polypeptides intranasally administered.

Despite these disadvantages, scientists have attempted to improve the absorption of compounds in the nasal cavity using a variety of techniques including: (1) adding bioadhesive polymers to intranasal formulations to increase the residence time of the formulation in the nasal cavity; (2) adding nontoxic enhancers to intranasal formulations to improve the permeability of the nasal cavity; and (3) using enzyme inhibitors to prevent the degradation of the peptides by various proteolytic enzymes in the nasal cavity.

One therapeutic agent which has been extensively studied for its ability to be administered intranasally is insulin. Insulin is the primary therapeutic agent used for the treatment of diabetes mellitus and in particular, type I diabetes. Currently, diabetes in mammals is often treated with daily parenteral injections of insulin. However, due to the local discomfort and the disruption in lifestyle resulting from daily hypodermic injections of insulin, many patients with diabetes refuse to accept the insulin therapy entirely. As a result, numerous investigators have attempted to find an effective method of administering insulin intranasally.

In 1932, Collins et al. studied the absorption of insulin through nasal mucous-membranes in diabetic patients. Collins et al. (1932) *Proc. Soc. Exp. Biol. Med.,* 29:756. In their study, insulin solutions containing saponin were sprayed by an atomizer or applied directly to the membranes of a diabetic patient using a small cotton pledget. Although a reduction in blood glucose levels following the intranasal administration of insulin to the diabetic patients was similar to the blood glucose levels found following a subcutaneous administration of insulin, the treatment produced mild congestion in the nasal mucosa and some symptoms of rhinitis.

In 1981, Hirai et al. compared glucose levels in rats following intranasal administration of insulin versus oral and intravenous administration of insulin. Hirai et al. (1981) *Int. J. Pharm.,* 9:173. Hirai et al. found that plasma glucose levels in rats intravenously administered insulin decreased significantly, while plasma glucose levels following oral administration only slightly decreased. To achieve normoglycemia, a larger dose of insulin was required when it was administered intranasally compared to the dose required for intravenous administration. Specifically, a 10-fold increase in concentration of insulin was required for the intranasal administration of insulin to reduce plasma glucose levels in the rats to levels similar to the levels found following a parenteral administration of insulin.

To further enhance the nasal absorption of insulin, previous studies have examined adding surfactants to insulin. For example, the intranasal administration of insulin containing the surf actant sodium glycocholate decreased blood glucose levels; however, the dose of insulin needed to achieve normoglycemia was approximately 3 to 4 times that of intravenous administration of insulin. Yokosuka et al. (1977) *J. Jpn. Diabet. Soc.,* 20:146.

The prior art discloses various methods for incorporating an additive or other active ingredient into a substrate, such as a polymer. One such method of incorporating (infusing) an additive into a polymeric material is described in U.S. Pat. No. 4,820,752 (Berens et al.) which employs a supercritical fluid, i.e., a gas at atmospheric pressure and temperature that becomes a liquid at below or equal to the critical temperature of the fluid. In U.S. Pat. No. 4,598,006 Sand employed this general method to impregnate a polymer with a fragrance, a pest control agent or scopolamine, all of which are of relatively low molecular weight. This method has not been employed incorporating a protein or a peptide in a polymer and administering such a protein or a peptide to a mammal through mucosa.

It has been surprisingly discovered in accordance with the present invention that peptides and proteins can be successfully infused into a matrix material and subsequently administered intranasally to treat various diseases in mammals without the addition of permeation enhancement compounds. The present invention alleviates many of the problems associated with the current methods of administering therapeutic agents intranasally to mammals by providing a pharmaceutical composition comprising a microparticle 10 to 250 μm in diameter containing a therapeutic agent and a pharmaceutically acceptable carrier. In particular, the present invention provides a pharmaceutical composition containing a microparticle which is produced by infusing a therapeutic agent, such as a peptide or protein, into a matrix material. The present invention further alleviates many of the problems encountered with intranasal liquid and spray preparations, such as chemical and microbiological instability during storage.

SUMMARY OF THE INVENTION

The present invention relates to a new and effective pharmaceutical composition comprising microparticles of a matrix having 0.1 to 500 μm and often preferably 10 to 250 μm in diameter. The microparticles may be produced by various known methods, some of which are described in greater detail below. Thereafter a therapeutic agent is infused into the matrix material. Optionally, a pharmaceutically-acceptable carrier may also be employed. In a preferred embodiment, the therapeutic agent is a peptide or protein.

The present invention further relates to a method of infusing a therapeutic agent into a matrix material in the form microparticles having 0.1 to 500 μm in diameter resulting in the particles absorbing or adsorbing said therapeutic agent. In particular, said therapeutic agent is infused into or onto said matrix material by (a) providing in a pressure vessel an intimate mixture of a therapeutic agent such as a protein or peptide with a matrix material; (b) contacting a compressed solvent, which is normally gaseous at ambient temperature and pressure, with said matrix material and said therapeutic agent in the pressure vessel under conditions effective to permit sorption of at least a portion of said therapeutic agent and said compressed solvent into said matrix material; (c) separating the solvent from the matrix material, thereby entrapping the protein or peptide. In a preferred embodiment, the therapeutic agent is a peptide or protein and the matrix material is polyacrylic acid or ammonium glycyrrhizinate.

The exact size of the particles of the matrix is not critical. As noted above, generally the particles may have a diameter of 0.1 to 500 μm, but particles of smaller or larger diameter may also be employed successfully. For example, if the matrix containing a therapeutic agent is to be administered by injection, it is preferable that the particles have small diameters, 0.1 μm or even less and up to about 1.0 μm. If the administration is through a mucosal membrane, it may be preferable to have a wider range of particle sizes, such as from 10 to 500 μm or from 10 to 250 μm. The selection of the range of the diameters of the matrix particles will depend on the specific material used as the matrix, the chemical nature and the molecular weight of the therapeutic agent and the manner of delivery to the mammal, i.e., is it injected or delivered through a mucosal membrane and the specific type of a membrane, such as, for example, nasal, vaginal or rectal.

Another aspect of this invention is directed to a method of treating or preventing a disease in a mammal by administering to a mammal a pharmaceutical composition through a mucous membrane. In a preferred embodiment, the therapeutic agent is a peptide or a protein. In a further preferred embodiment, said therapeutic agent in said pharmaceutical composition is infused by the method described by the present invention.

The present invention further provides an article of manufacture comprising a packaging material and a microparticle contained within said packaging material.

DETAILED DESCRIPTION OF INVENTION

Figure 1:
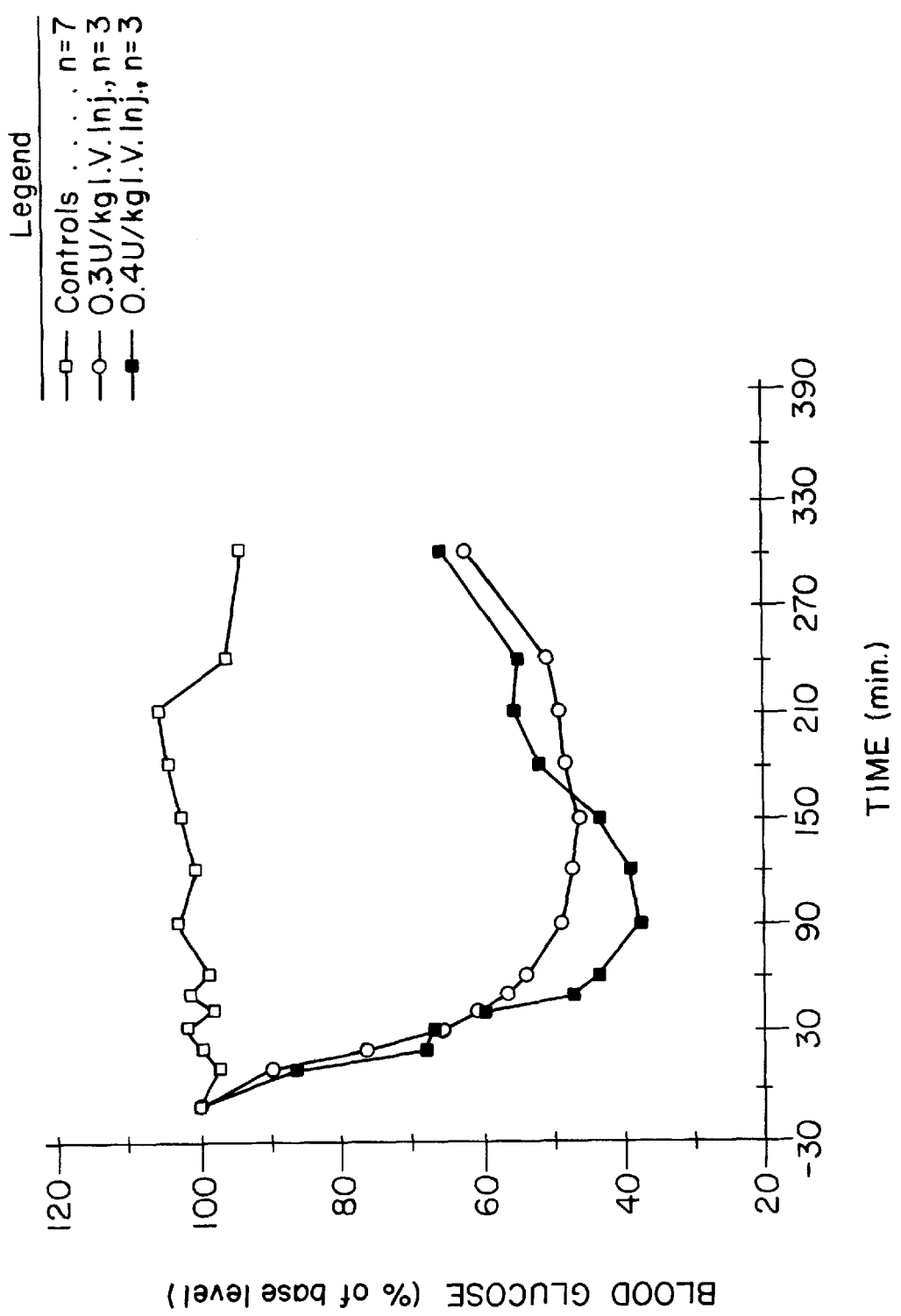
FIG. 1 shows the blood glucose reduction following an intravenous injection of insulin (0.3 and 0.4 U/kg) in diabetic rabbits.

There has been discovered in accordance with the present invention a unique pharmaceutical composition which can comprise any of a large variety of therapeutic agents and which, when administered intranasally to a mammal, effectively treats the disease or disorder in a mammal against which the therapeutic agent is directed, without the addition of a permeation enhancer. Specifically, the present invention is directed to a pharmaceutical composition comprising microparticles 10 to 250 μm in diameter, which are produced by infusing a therapeutic agent into a matrix material and, optionally, a pharmaceutically-acceptable carrier.

In accordance with the present invention, the microparticles comprise a therapeutic agent infused into a matrix material. As used herein, the term "matrix material" denotes a polymer or any other substance with a molecular structure whereby a therapeutic agent can readily be diffused or infused into and be held within or on said matrix material prior to administration. Applicants do not wish to be limited by any specific theory, but it is believed that the therapeutic agent is infused into the matrix or absorbed by the matrix and thereafter held within the crevices of the matrix by some physical means, such as through hydrogen bonding or some forces that attract each other. Upon administration to a mammal mucous membrane, such as intranasal administration, said therapeutic agent can slowly diffuse from said matrix material into the mammal whereupon said therapeutic agent is biologically active. Examples of matrix materials which the microparticles in accordance with the present invention comprise include, for example, ammonium glycyrrhizinate, polyacrylic acid, polyethylene oxide, chitosan, algin, saturated polyglycolysed glyceride, glycerol palmitostearate, saturated $C_{12}$ to $C_{22}$ fatty acid esters of polyalcohol, glyceryl and polyethylene glycol behenate and cross-linked polyacrylic acid. In a preferred embodiment, the saturated polyglycolysed glyceride is GELUCIRE®, the glycerol palmitostearate is PRECIROL®, the saturated $C_{12}$ to $C_{22}$ fatty acid esters of polyalcohol is LUBRIFIAN®, and the glyceryl and polyethylene glycol behenate is COMPRITOL®, all of which are distributed by Gattefosse, 36 chemin de Genas, 69800 Saint-Priest, France. GELUCIRE® is composed of saturated polyglycolysed glycerides. The compound is soluble in chloroform and insoluble in ethanol at 20° C. PRECIROL® is atomized glycerol palmitostearate made of mono, di and triglycerides of saturated fatty acids $C_{16}$ and $C_{18-}$. The compound is freely soluble in chloroform and insoluble in ethanol at 20° C. LUBRIFIANT® is composed of saturated $C_{12}$ to $C_{22}$ fatty acid esters of polyalcohol. The compound is very soluble in chloroform at 20° C. and soluble in ethanol at 35–40° C. COMPRITOL® is composed of glyceryl and polyethylene glycol behenate. The compound is freely soluble in chloroform and insoluble in ethanol at 20° C. In a preferred embodiment, the matrix material is polyacrylic acid or ammonium glycyrrhizinate.

The microparticles used as the matrix in the present invention can be produced using a variety of conventional techniques. For example, a microparticle may be produced by forming a solution of monomers containing methacrylic acid (30 mL), 5 mol % triethyleneglycol dimethyacrylate and 0.3 g $K_2SO_4$ in 400 ml deionized water and heating the monomer solution to between 95–100° C. During the heating process, the monomer solution is stirred continuously and placed under nitrogen gas for approximately two hours. Following this process, a viscous mass is formed which is vacuum dried at 50° C. for two days. The cross-linked polymer is mechanically ground using a conventional grinder to produce the desired particle size of the microparticles. The microparticles produced are extracted three times with hot water and then redried. The microparticles formed using the method described have a diameter ranging from 10 to 250 μm. In a preferred embodiment, the diameter of the microparticles is from 30 to 100 μm.

The therapeutic agent to be infused into the matrix material must be able to diffuse into the matrix material and remain in said matrix material until administered to a mammal intranasally or through some other mucosal membrane. Once administered, said therapeutic agent must retain its biologic activity and be capable of diffusing into the membranes of the recipient. In accordance with the present invention, therapeutic agents which can be infused into the matrix material include preferably proteins and peptides such as, for example, insulin, calcitonin, atrial naturetic peptide, glucagen, nifedipine, testosterone, progesterone, vitamin B-12, propranalol, chlorpropamide, morphine, bupromorphine, muramyl dipeptides, secretin, cholecystokinin, thyrotropin-releasing-hormone (TRH), thymopentin, adrenocorticotropic hormone, growth hormone releasing factor, enkephalin, oxytocin, vaasopressin,a dn luteinizing hormone releasing hormone.

In a preferred embodiment, the therapeutic agent is a peptide or protein. As defined by the present invention, a peptide is a molecule which is a compound composed of two or more amino acids joined by peptide bonds with a molecular weight ranging from 100 to 1000 daltons and which, when administered to a mammal, effectively treats a particular disease to which the peptide is directed. A protein, as used herein, is a polypeptide compound with a molecular weight of not less than 1,000 daltons, often over 6,000, and not greater than 100,000 daltons and is similarly an effective treatment for a particular disease in a mammal to which the protein is directed. Examples of therapeutic agents which are peptides—and proteins that can be infused into the matrix material described by the present invention include, for example, insulin, glucagen, calcitonin, atrial naturetic peptide, muramyl dipeptides, secretin, cholecystokinin, thyrotrophin releasing hormone, thymopentin, adrenocorticotropic hormone, growth hormone releasing factor, enkephalin, oxytocin, vasopressin, and luteinizing hormone releasing hormone. In a further preferred embodiment, the therapeutic agent is insulin.

There are several unique and unexpected features of this invention involving the infusion or incorporation of a protein or peptide employing a supercritical fluid by a method described herein. One such important feature is that infusion of a protein or peptide can be accomplished without causing agglomeration of the matrix particles. If other known methods of infusing a therapeutic agent into matrix particles is employed, agglomeration of the particles usually occurs during the infusion step and then it is necessary to grind the material to obtain the desired particle size distribution. Proteins and peptides cannot withstand the heat generated during the grinding step. The method of this invention permits to obtain the desired particle size distribution prior to the infusion step and such particle size distribution remains substantially the same after the infusion step without the need for further processing. Thus this invention enables one to infuse or incorporate a protein or a peptide into or onto a matrix material to protect the protein or peptide from premature decomposition or destruction by the body and delivering a protein or a peptide to a mammal by placing the matrix, containing the infused protein or a peptide, next to or in the vicinity of a mucosal membrane of a mammal. The matrix containing a protein or peptide may be administered in the form of a liquid or solid spray or by other appropriate methods known in the art.

The therapeutic agent, such as a protein or peptide, is administered to a mammal by way of a mucous membrane or surface such as nasal, buccal, sublingual, vaginal, rectal and possibly corneal if the composition as a whole is non-irritating and otherwise safe to the eye. One of the more practical methods of administration is nasal.

A pharmaceutically-acceptable carrier, which could be a liquid or a solid, as defined by the present invention, may be optionally employed. This permits a convenient delivery to a mammal of the therapeutic agent contained within the microparticles through mucosa, such as intranasally. There is not necessarily any bonding interaction between the pharmaceutically acceptable carrier and the microparticle; the microparticles are simply suspended or dispersed in the carrier. The carrier containing the matrix particles that have been infused with a protein or a peptide, can be sprayed into a nose, mouth, rectum or vagina to deliver the active ingredient to a mammal. The pharmaceutically-acceptable carrier in which the microparticles are suspended or dispersed may be any solvent or solid that is non-toxic to the mammal and does not affect the bioactivity of the microparticle. Suitable pharmaceutically-acceptable carriers include liquid carriers, such as normal saline or other non-toxic solutions at or near physiological concentrations, and solid carriers, such as sucrose or manitol. Additional examples of suitable carriers are well-known in the art.

A further aspect of this invention is directed to a method of infusing a therapeutic agent into a matrix material to produce microparticles containing said therapeutic agent. By "infusing" is meant incorporating, embedding or impregnating a therapeutic agent in the matrix microparticles. The method of infusing a therapeutic agent into a matrix material is described in U.S. Pat. Nos. 4,820,752 and 4,598,006. This method comprises the steps of: (a) providing in a pressure vessel an intimate mixture of a therapeutic agent with a matrix material; (b) contacting a compressed solvent, which is normally gaseous at ambient temperature and pressure, with said matrix material and said therapeutic agent in the pressure vessel under conditions effective to permit sorption of at least a portion of said therapeutic agent and said compressed solvent into said matrix material; and (c) removing and separating said solvent from said matrix material, thereby entrapping the infused therapeutic agent. As defined by the present invention, a pressure vessel is a conventional apparatus used by one of ordinary skill in the art to exert pressure on a substance which is greater or less than ambient pressure.

As used herein, the term "solvent" refers to a fluid with a boiling point below room temperature (22° C.) when measured at atmospheric pressure (14.7 psi, 101.3 kPa). It is well known in the art that all fluids possess a critical temperature above which a gaseous fluid cannot be converted to a liquid regardless of the pressure exerted on the gaseous fluid. Thus, the ability of a given fluid to be an effective solvent increases as the density of the gaseous fluid increases. The solvent used in accordance with the present invention may be compressed at temperatures above, equal to, or below the critical temperature of the solvent. When the solvent is compressed above its critical temperature, the solvent is in a supercritical or gaseous state. When the solvent is compressed at or below its critical temperature, the solvent is in a liquid state. The therapeutic agents used in the infusion method described by the present invention must be soluble in the compressed solvent when in its liquid or critical state.

The compressed solvent used to infuse the therapeutic agent into the matrix material according to the method described by the present invention may be, for example, carbon dioxide, nitrous oxide, ethylene, ethane, monochlorotrifluoromethane, acetylene, phosphine, hydrogen chloride, fluoroform, sulphur dioxide, methane, methyl fluoride, or phosphonium chloride. In a preferred embodiment, the solvent is carbon dioxide.

The matrix material into which the therapeutic agent is infused using the process described by the present invention may be, for example, ammonium glycyrrhizinate, polyacrylic acid, polyethylene oxide, chitosan, algin, saturated polyglycolysed glyceride, glycerol palmitostearate, saturated $C_{12}$ to $C_{22}$ fatty acid esters of polyalcohol, glyceryl and polyethylene glycol behenate or cross-linkedpolyacrylic acid. In a preferred embodiment, the matrix material is polyacrylic acid or ammonium glycyrrhizinate.

The therapeutic agent which may be infused into the matrix material must have some degree of solubility in said matrix material. In a preferred embodiment, the therapeutic agent has a degree of solubility in the matrix material of at least 0.1 percent by weight. However, it may be possible to infuse into a matrix and the matrix retain a therapeutic agent if the therapeutic is not actually soluble in the matrix but the particles of the therapeutic agent have some weak association with the particles of the matrix, such as by hydrogen bonding or dipole forces, which would result in the therapeutic agent remaining within the matrix after the solvent (the supercritical fluid) has been removed from the matrix. In accordance with the present invention, therapeutic agents which can be infused into the matrix material include, for example, insulin, calcitonin, atrial naturetLc peptide, glucagon, nifedipine, testosterone, progesterone, vitamin B-12, propranalol, chlorpropamide, morphine, bupromorphine, muramyl dipeptides, secretin, cholecystokinin, thyrotrophin releasing hormone, thymopentin, adrenocorticotropic hormone, growth hormone releasing factor, enkephalin, oxytocin, vasopressin, and luteinizing hormone releasing hormone.

In a preferred embodiment, the therapeutic agent is a peptide or protein. Examples of therapeutic agents which are peptides and proteins which can be infused into the matrix material described by the present invention include, for example, insulin, glucagon, calcitonin, atrial naturetic peptide, muramyl dipeptides, secretin, cholecystokinin, thyrotrophin releasing hormone, thymopentin, adrenocorticotropic hormone, growth hormone releasing factor, enkephalin, oxytocin, vasopressin, and luteinizing hormone releasing hormone. In a further preferred embodiment, the therapeutic agent is insulin.

The therapeutic agent can be solubilized into the solvent following liquefaction of the solvent, or it can be placed into a pressure vessel whereupon the solvent material is added and compressed. According to the method of infusion described by the present invention, if the solution of therapeutic agent is infused into the matrix material at a temperature at or below the critical temperature of the solvent, the pressure in the pressure vessel is at least 10% of the saturated vapor pressure of the fluid solvent. If the therapeutic agent is infused at a temperature above the critical temperature of the solvent, the pressure in the vessel is at least 0.5 to 5 times that of the critical pressure of the fluid solvent. The therapeutic agent and the solvent are maintained in contact with the matrix material for a period of time sufficient to permit a desired amount of the matrix material to be dispersed in the matrix material.

According to the method of the present invention, the therapeutic agent dispersed or dissolved in the solvent is maintained in contact with the matrix material for a time sufficient for the desired amount of the therapeutic agent to infuse into the matrix material. In particular, the amount of therapeutic agent that is infused into the matrix material ranges from 0.1 to 40 wt. % of the matrix material. The solvent is compressed to a density of at least 0.01 g/cc either before or after being introduced into the pressure vessel. In a preferred embodiment, the solvent is compressed to a density of at least 0.1 g/cc.

Following infusion, the matrix material is separated from any remaining solvent using any of a variety of techniques including high pressure centrifuge separation, filtration or venting the pressure vessel. Reducing the pressure within the pressure vessel to atmospheric pressure causes the fluid solvent to diffuse from the polymer, thereby entrapping the therapeutic agent within the matrix material.

In a preferred embodiment of the present invention, the therapeutic agents are infused into the matrix material as provided in U.S. Pat. No. 4,820,752 to Berens et al.

Another aspect of the present invention provides a method of treating or preventing a disease in a mammal by intranasally administering to said mammal an effective amount of a pharmaceutical composition, comprising microparticles prepared in accordance with the present invention and containing a therapeutic agent which effectively treats the disease or disorder against which the therapeutic agent is directed. The method of treating or preventing a disease or disorder in a mammal described by the present invention solves many of the problems associated with conventional therapeutic techniques for treating or preventing various diseases and disorders in mammals. Unlike the therapies described in the prior art, the method of treating or preventing diseases described by the present invention is noninvasive, maintains the bioactivity of the therapeutic agent in the matrix material and does not result in adverse side effects associated with conventional intranasal pharmaceutical compositions containing absorption enhancers such as surfactants.

The pharmaceutical composition defined by the present invention is intranasally administered to a mammal using a conventional spray device to disperse the microparticles into the mammal's nasal cavity.

Examples of diseases which can be treated or prevented using the method described by the present invention include, for example, diabetes mellitus, hormone insufficiency, high blood pressure, bacterial and viral infections, renal insufficiency, complement cascade deficiency and rheumatic disorders.

The present invention further provides an article of manufacture comprising a packaging material and a pharmaceutical composition contained within said packaging material, wherein said pharmaceutical composition contains microparticles prepared in accordance with the present invention and containing a therapeutic agent infused, as taught herein, into a matrix material and a pharmaceutically acceptable carrier and wherein said packaging material contains a label that indicates that said pharmaceutical composition can be used to prevent or treat a disease in a mammal. The packaging material used to contain the pharmaceutical composition can comprise glass, plastic, metal or any other suitably inert material.

In order to further illustrate the present invention, the experiments described in the following examples were carried out. It should be understood that the invention is not limited to the specific examples or the details described therein. The results obtained from the experiments described in the examples are shown in the accompanying figures.

EXAMPLE I

Method of Infusing Insulin into a Matrix Material

Two representative matrix materials, ammonium glycyrrhizinate and polyacrylic acid, were infused with a representative therapeutic agent, human insulin, or were freeze-dried with human insulin. The diameter of the matrix material prior to the infusion process ranged from 20 to 250 urn. Approximately 475 mg of the matrix material, ammonium glycyrrhizinate or polyacrylic acid, was mixed with 25 mg insulin for 10 minutes in a glass vial. The glass vial containing the matrix material/insulin was placed into a pressure vessel and air inside the vessel was slowly replaced with $CO_2$. Carbon dioxide, at room temperature (20° C.), was added to a pressure of 950 psi and maintained. The contents were held in the vessel at room temperature for up to 24 hours, following which the pressure in the vessel was slowly released. The microparticles produced by this infusion process were removed from the pressure vessel, placed in a desiccator and stored in a refrigerator. The microparticles contain 5 wt % of insulin. This was determined by an acceptable high-pressure liquid chromatography (HPLC) analytical method.

Microparticles containing insulin by freeze-drying were produced by hydrating the matrix material, polyacrylic acid or ammonium glycyrrhizinate, in a glass vial with an isotonic insulin phosphate solution with a pH of 7.5. The glass vials were placed in a refrigerator for 12 hours at -5° C. Following refrigeration for 12 hours, the vials were placed in a freezer at -20° C. for one hour. The glass vials were then placed in a lyophilizer under vacuum at 5 to 10 $\mu$mHg and at a temperature of -50° C. for 24 hours. The vials were removed from the lyophilizer and the microparticles were placed in a desiccator and stored in a refrigerator.

EXAMPLE II

Comparison of Nasal and Intravenous Administration of Insulin in Diabetic Rabbits This study investigated the hypoglycemic effect on diabetic rabbits following the intranasal administration of ammonium glycyrrhizinate or polyacrylic acid infused with insulin. Insulin was infused into the carrier using essentially the same procedure described in Example I.

The animals used in this study were Male New Zealand White rabbits weighing approximately 2.5 kg. (Charles River Labs, Amherst, Mass.). The animals were housed individually in cages and given standard animal chow and water. All animals were treated according to the Guiding Principles for Laboratory Animal Care of the American Physiologic Society.

The animals were made diabetic by intravenously injecting 80 mg/kg of Alloxan suspended in isotonic saline solution into the animal. The animals' blood glucose levels were monitored every two to three hours for the first three days. When glucose levels reached 500 mg/dl during the first three days, insulin (0.15 U/kg) was administered. After the animals were made diabetic, in vivo experiments were run to study the effect of intranasally administering ammonium glycyrrhizinate or polyacrylic acid infused with insulin on the diabetic rabbits.

Prior to the experiment, the animals were fasted for 16 hours. The animals were then anesthetized by intravenously administering 30 mg/kg sodium pentobarbital. Forty minutes following the initial dose of pentobarbital, a second dose (6 mg/kg) was administered to the animals. While the animal was under anesthesia, a catheter was placed in the rabbits ear artery and held in place with surgical tape.

The animals were placed into groups of 3 to 7 animals for each experiment. All tests were run in duplicate. Blood glucose levels and serum insulin levels were measured for each experiment. Insulin, when administered, was administered intravenously or intranasally using a powder insufflator (Miat, Italy).

To monitor the blood glucose levels, 0.5 to 0.8 ml of blood were collected from each animal through the catheter at time intervals of −15, −10, 10, 20, 30, 40, 50, 60, 90, 120, 150, 180, 210, 240 and 300 minutes after the initial dose of the therapeutic agent. Blood glucose were assayed immediately after the blood samples were collected using a ChemStrip bG Test Strip and a Accu Chek II Blood Glucose Monitor.

Following the blood glucose analysis, serum samples were obtained by centrifuging the blood samples collected at 3000 rpm for 10 minutes. The serum samples were stored at 600 c until assayed for serum insulin levels. Serum insulin levels were determined using radio immune assay kits. The detection limit for the assay kits used was below 2 uu/ml.

Figure 2:
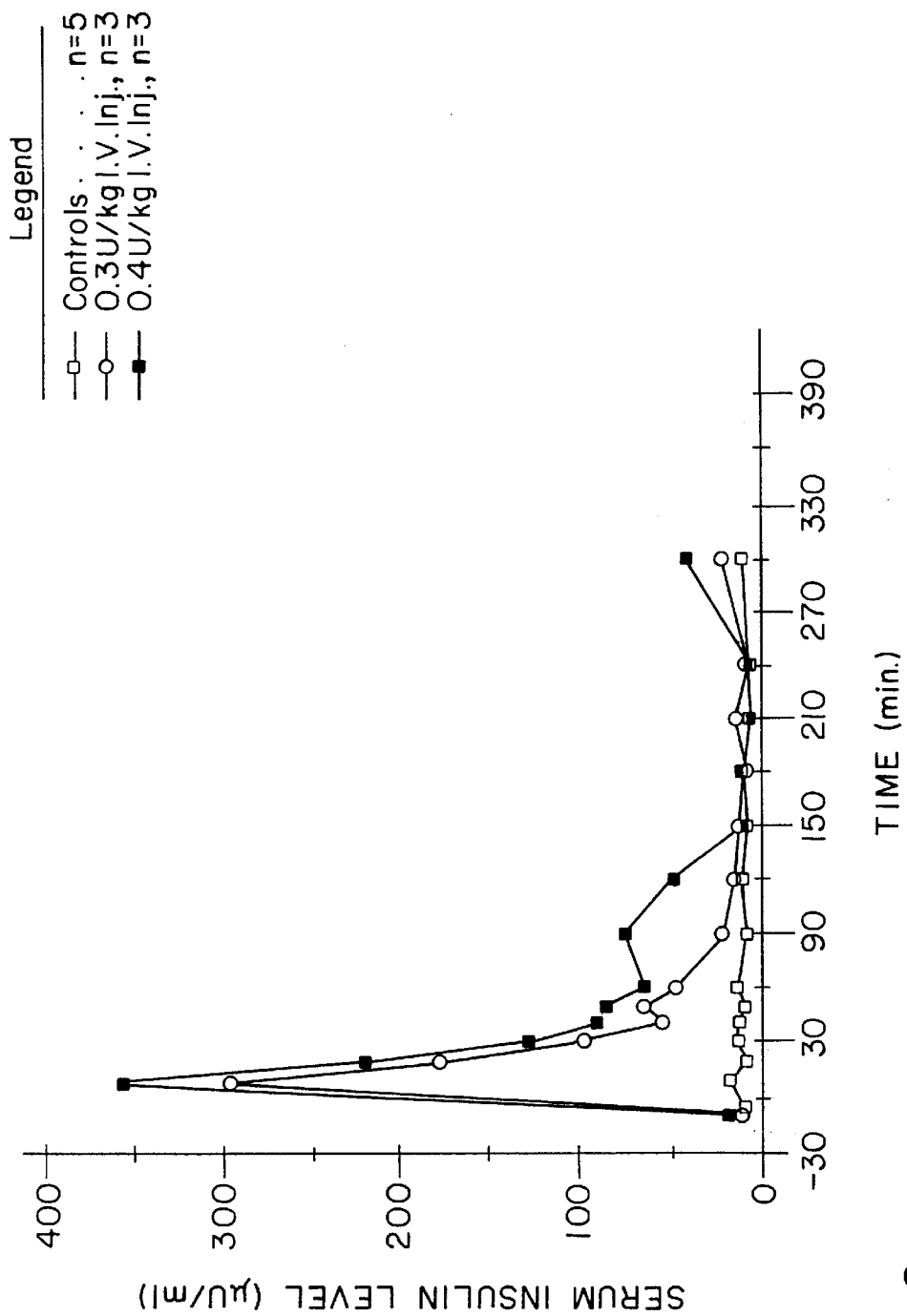
FIG. 2 shows the serum insulin levels following an intravenous injection of insulin (0.3 and 0.4 U/kg) in diabetic rabbits.

FIG. 1 shows the blood glucose levels for three groups of diabetic rabbits following an intravenous injection of insulin or saline at time intervals −30 to 300 minutes after the injection. The group of animals intravenously administered 0.3 and 0.4 U/kg insulin showed a fall in blood glucose levels while the control group, administered saline solution, showed no fall in blood glucose levels as shown in FIG. 1. The corresponding insulin levels for the three groups of animals are shown in FIG. 2. As shown in FIGS. 1 and 2, the serum insulin levels increased as the blood glucose levels fell. This data represent the classic response in blood glucose levels following the administration of insulin.

Figure 3:
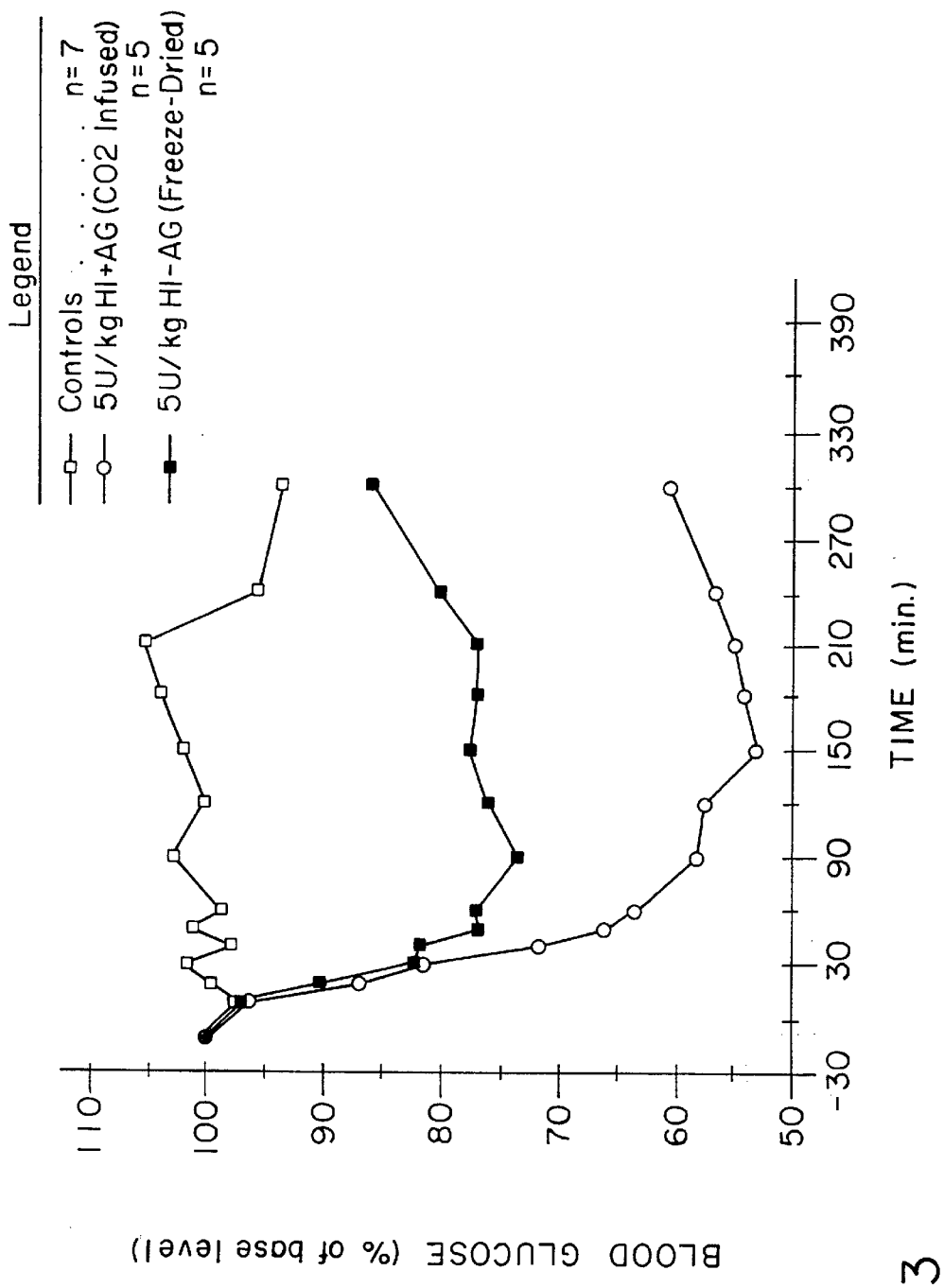
FIG. 3 shows the hypoglycemic effect following the intranasal administration of ammonium glycyrrhizinate infused with insulin (5 U/kg) and freeze-dried with insulin (5 U/kg) in diabetic rabbits.
Figure 4:
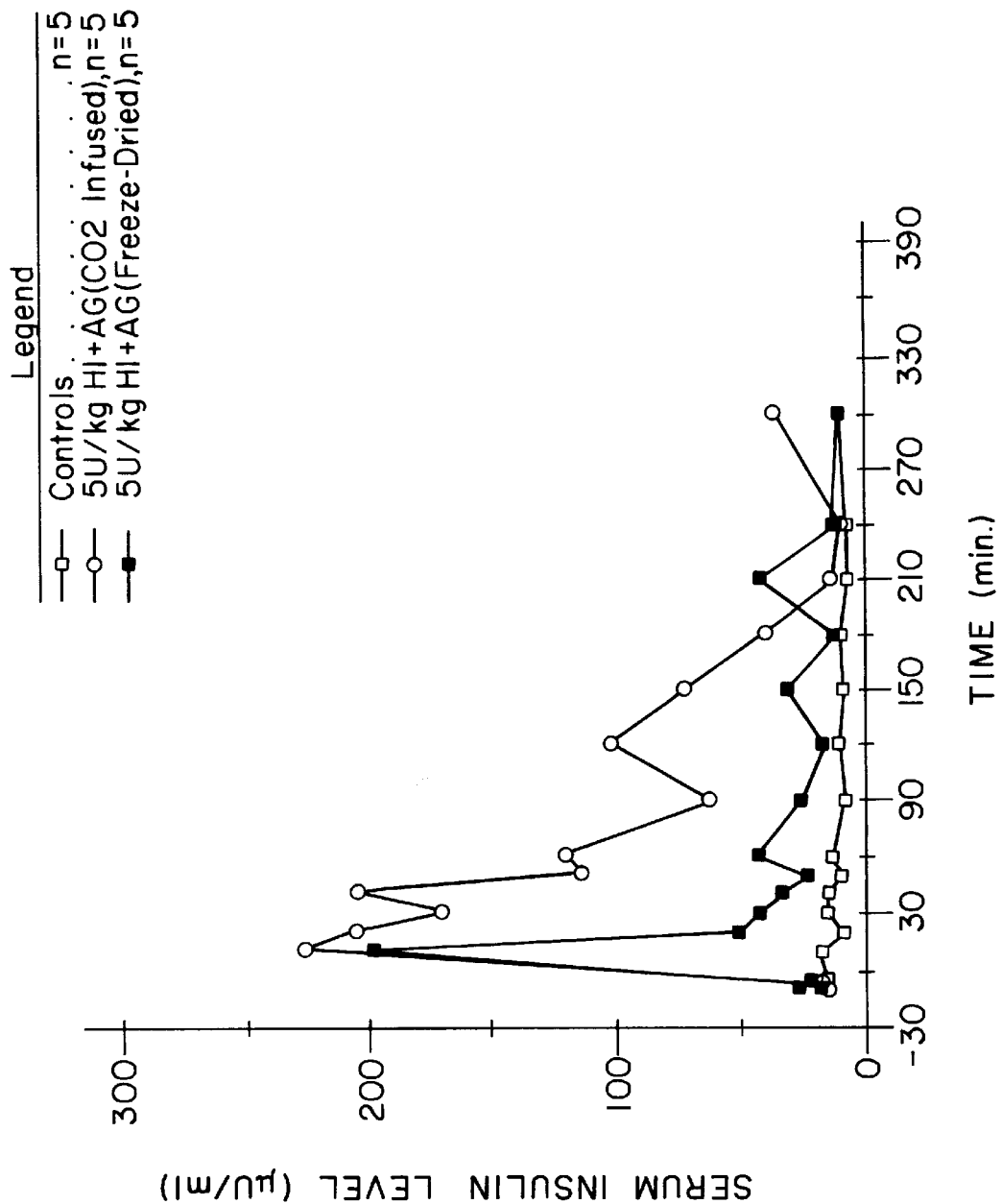
FIG. 4 shows serum insulin levels following the intranasal administration of ammonium glycyrrhizinate infused with insulin (5 U/kg) and ammonium glycyrrhizinate freeze-dried with insulin (5 U/kg) in diabetic rabbits.

FIG. 3 shows the hypoglycemic effect following intranasally administering ammonium glycyrrhizinate infused with 5 U/kg insulin and ammonium glycyrrhizinate freeze-dried with insulin. The corresponding serum insulin levels are shown in FIG. 4. As shown in FIG. 3, animals intranasally administered ammonium glycyrrhizinate infused with insulin as described in Example I showed a reduction in their blood glucose levels comparable to the reduction achieved by intravenously injecting 0.4 U/kg insulin. In contrast, animals intranasally administered freeze-dried insulin showed only a slight reduction in blood glucose levels.

The corresponding serum insulin levels following the intranasal administration of ammonium glycyrrhizinate infused with insulin showed a reduction in insulin over time. This data illustrates the efficacy of intranasally administering ammonium glycrrhizinate infused with a therapeutic agent to treat the respective disease.

Figure 5:
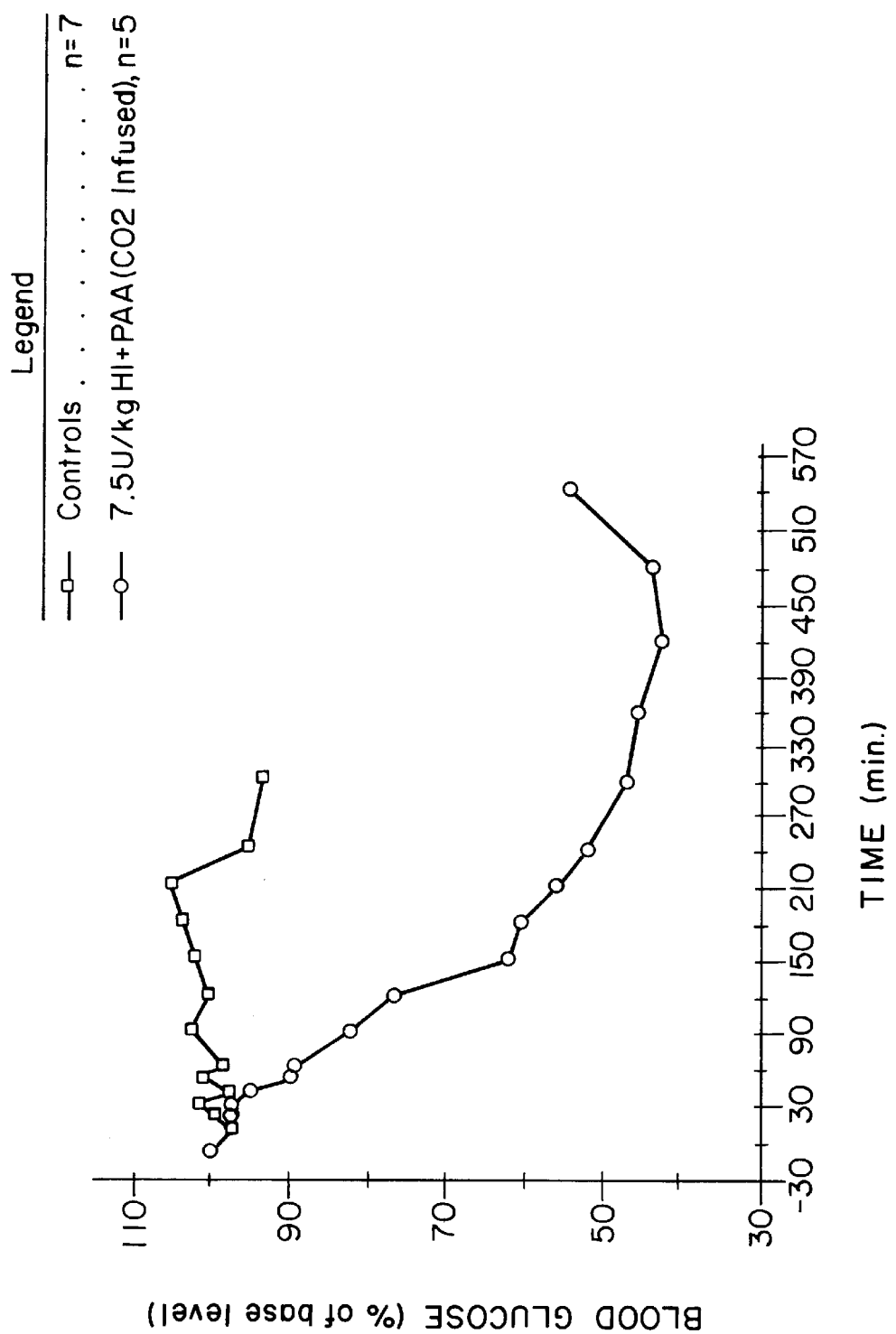
FIG. 5 shows the hypoglycemic effect following the intranasal administration of polyacrylic acid infused with insulin (7.5 U/kg) in diabetic rabbits.
Figure 6:
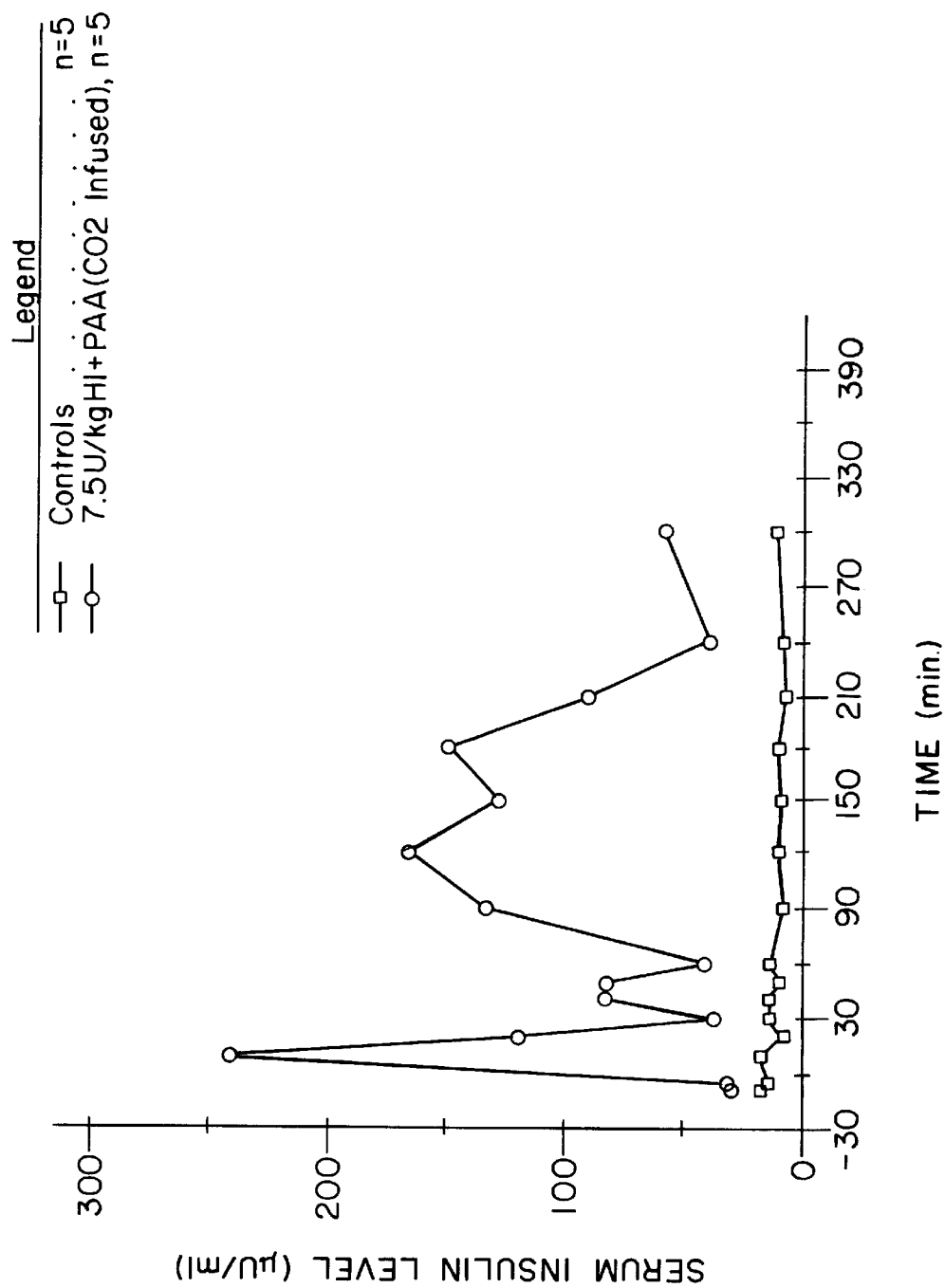
FIG. 6 shows the serum insulin levels following the intranasal administration of polyacrylic acid infused with insulin (7.5 U/kg) in diabetic rabbits.

Diabetic rabbits intranasally administered polyacrylic acid infused with insulin as described in Example 1 similarly showed a reduction in blood glucose levels to normoglycemia as shown in FIG. 5. The corresponding serum insulin concentration is shown in FIG. 6. These studies similarly show the ability of a pharmaceutical composition described by the present invention to treat a disease in a mammal by intranasally administering said pharmaceutical composition.

We claim:

1. A pharmaceutical composition comprising a matrix material selected from the group consisting of chitosan, algin, saturated polyglycolysed glyceride, glycerol palmitostearate, saturated $C_{12}$ to $C_{22}$ fatty acid esters of polyalcohol, glyceryl and polyethylene glycol behenate, polyethylene oxide, and ammonium glycyrrhizinate in the form of microparticles containing a protein or peptide selected from the group consisting of insulin, glucagons, calcitonin, atrial naturetic peptide, muramyl dipeptides, secretin, cholecystokinin, thyrotrophin releasing hormone, thymopentin, adrenocorticotripic hormone, growth hormone releasing factor, enkephalin, oxytocin, vasopressin and luteinizing hormone releasing hormone said composition being produced by infusing into or onto said matrix material by:

(a) providing in a pressure vessel an intimate mixture of said protein or peptide with the particles of the matrix material;

(b) contacting a compressed solvent, which is normally gaseous at ambient temperature and pressure, with said matrix material and said protein and peptide in the pressure vessel under conditions effective to permit sorption of at least a portion of said protein or peptide and said compressed solvent into said matrix material;

(c) separating said solvent from said matrix material, thereby entrapping the infused protein or peptide.

2. A composition of claim 1, wherein said matrix particles have a diameter of from 0.1 to 500 $\mu$m.

3. A composition of claim 1, wherein the peptide or protein is insulin or a human growth hormone.

4. The pharmaceutical composition of claim 1, wherein said matrix material is polyacrylic acid or ammonium glycyrrhizinate.

5. The pharmaceutical composition of claim 4 wherein said microparticles are 30 to 100 $\mu$m in diameter.

6. A method of infusing a therapeutic agent selected from the group consisting of insulin, glucagons, calcitonin, atrial naturetic peptide, muramyl dipeptides, secretin, cholecystokinin, thyrotrophin releasing thymopentin, adrenocorticotripic hormone, growth hormone releasing factor, enkephalin, oxytocin, vasopressin and luteinizing hormone releasing hormone said composition being into a matrix material selected from the group consisting of chitosan, algin, saturated polyglycolysed glyceride, glycerol palmitostearate, saturated $C_{12}$ to $C_{22}$ fatty acid esters of polyalcohol, glyceryl and polyethylene glycol behenate, polyethylene oxide, and ammonium glycyrrhizinate wherein said method comprises:

(d) providing in a pressure vessel an intimate mixture of said therapeutic agent with a matrix material;

(e) contacting a compressed solvent, which is normally gaseous at ambient temperature and pressure, with said matrix material and said protein or peptide in the pressure vessel under conditions effective to permit sorption of at least a portion of said protein or peptide and said compressed solvent into said matrix material;

(f) separating said solvent from said matrix material, thereby entrapping the protein or peptide in the matrix.

7. The method of claim 6 wherein said matrix material is selected from the group consisting of polyacrylic acid, cross-linked polyacrylic acid, chitosan, algin, saturated polyglycolysed glyceride, glycerol palmitostearate, saturated $C_{12}$ to $C_{22}$ fatty acid esters of polyalcohol, glyceryl and polyethylene glycol behenate, polyethylene oxide and ammonium glycyrrhizinate.

8. The method of claim 7 wherein said matrix material is polyacrylic acid or ammonium glycyrrhizinate.

9. The method of claim 8 wherein said solvent is separated from said matrix material by venting the pressure vessel whereby said solvent evaporates.

10. The method of claim 6 wherein said protein or peptide is selected from the group consisting of insulin, glucagen, calcitonin, atrial naturetic peptide, muramyl dipeptides, secretin, cholecystokinin, thyrotrophin releasing hormone, thymopentin, adrenocorticotropic hormone, growth hormone releasing factor, enkephalin, oxytocin, vasopressin, and luteinizing hormone releasing hormone.

11. The method of claim 10 wherein said peptide or protein is insulin.

12. The method of claim 6 wherein said protein or peptide has a degree of solubility in the matrix material of at least 0.1 percent by weight.

13. The method of claim 6 wherein said solvent is carbon dioxide.

14. A method of protecting and delivering a protein or peptide selected from the group consisting of insulin, glucagons, calcitonin, atrial naturetic peptide, muramyl dipeptides, secretin, cholecystokinin, thyrotrophin releasing hormone, thymopentin, adrenocorticotripic hormone, growth hormone releasing factor, enkephalin, oxytocin, vasopressin and luteinizing hormone releasing hormone said composition being to a mammal, said method comprising;

(a) providing in a pressure vessel an intimate mixture of said protein or peptide with particles of a matrix material selected from the group consisting of chitosan, algin, saturated polyglycolysed glyceride, glycerol palmitostearate, saturated $C_{12}$ to $C_{22}$ fatty acid esters of polyalcohol, glyceryl and polyethylene glycol behenate, polyethylene oxide, and ammonium glycyrrhizinate;

(b) contacting a compressed solvent, which is normally gaseous at ambient temperature and pressure, with said matrix material and said protein or peptide in the pressure vessel under conditions effective to permit sorption of at least a portion of said protein or peptide and said compressed solvent into said matrix material;

(c) separating said solvent from said matrix material, thereby entrapping the protein or peptide in the matrix; and (d) delivering said protein or peptide to a mammal by placing said matrix infused with a protein or peptide adjacent to or in the vicinity of a mucosal membrane of a mammal.

15. A method of claim 14, wherein said matrix is polyacrylic acid or ammonium glycyrrhizinate and protein or peptide is insulin or growth hormone.

16. A method of treating or preventing a disease in a mammal comprising intranasally administering to said mammal an effective amount of a pharmaceutical composition of claim 1, which comprises a therapeutic agent effective to prevent or treat said disease.

17. The method of claim 16 wherein said disease is selected from the group consisting of diabetes mellitus, hormone insufficiency, high blood pressure, bacterial and viral infections, renal insufficiency, complement cascade deficiency and rheumatic disorders.

18. An article of manufacture comprising a packaging material and a microparticle contained within said packaging material, wherein said microparticle comprises a matrix material into which a therapeutic agent has been infused according to the method of claim 6, and wherein said packaging material contains a label that indicates that said microparticle can be used to prevent or treat a disease in a mammal.

19. A composition of claim 5, wherein the solvent is carbon dioxide.

20. A composition of claim 1 wherein a protein or peptide is dispersed in said solvent.

21. A composition of claim 1 wherein a protein or peptide is dissolved in said solvent.

22. A composition of claim 1 wherein from 0.1 to 40 weight percent of a protein or peptide, based on the weight of the matrix, is in the matrix.

23. A method of claim 6 wherein a therapeutic agent is dispersed in said solvent.

24. A method of claim 6 wherein a therapeutic agent is dissolved in said solvent.

25. A method of claim 6 wherein from 0.1 to 40 weight percent of a therapeutic agent, based on the weight of the matrix, is infused into the matrix.

* * * * *